United States Patent
Simon et al.

(10) Patent No.: US 9,174,049 B2
(45) Date of Patent: Nov. 3, 2015

(54) SYSTEMS AND METHODS FOR ELECTRICAL STIMULATION OF SPHENOPALATINE GANGLION AND OTHER BRANCHES OF CRANIAL NERVES

(71) Applicant: ElectroCore, LLC, Basking Ridge, NJ (US)

(72) Inventors: Bruce J. Simon, Mountain Lakes, NJ (US); Joseph P. Errico, Warren, NJ (US)

(73) Assignee: Electrocore, LLC, Basking Ridge, NJ (US)

( * ) Notice: Subject to any disclaimer, the term of this patent is extended or adjusted under 35 U.S.C. 154(b) by 0 days.

(21) Appl. No.: 14/164,927

(22) Filed: Jan. 27, 2014

(65) Prior Publication Data

US 2014/0214120 A1   Jul. 31, 2014

Related U.S. Application Data

(60) Provisional application No. 61/757,200, filed on Jan. 27, 2013.

(51) Int. Cl.
| | | |
|---|---|---|
| *A61N 1/00* | (2006.01) | |
| *A61N 1/36* | (2006.01) | |
| *A61N 1/05* | (2006.01) | |
| *A61N 1/378* | (2006.01) | |
| *A61N 1/372* | (2006.01) | |

(52) U.S. Cl.
CPC .......... *A61N 1/36075* (2013.01); *A61N 1/0546* (2013.01); *A61N 1/3787* (2013.01); *A61N 1/37205* (2013.01); *A61N 1/37229* (2013.01)

(58) Field of Classification Search
CPC .............. A61N 1/0546; A61N 1/3605; A61N 1/36075; A61N 1/36017; A61M 15/08
See application file for complete search history.

(56) References Cited

U.S. PATENT DOCUMENTS

| | | |
|---|---|---|
| 3,590,810 A | 7/1971 | Kopecky |
| 4,196,737 A | 4/1980 | Bevilacqua |
| 5,458,141 A | 10/1995 | Neil |
| 5,899,922 A | 5/1999 | Loos |
| 5,983,131 A | 11/1999 | Weaver et al. |
| 6,341,236 B1 | 1/2002 | Osorio et al. |

(Continued)

FOREIGN PATENT DOCUMENTS

| | | |
|---|---|---|
| WO | WO 93/01862 | 2/1993 |
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Robert N Wieland
(74) *Attorney, Agent, or Firm* — Dentons US LLP

(57) ABSTRACT

Devices, systems and methods are disclosed for modulating cranial nerves, such as the sphenopalatine ganglion, to treat a medical condition of a patient, such as cluster headache. A stimulation device is advanced transnasally to a target site at or adjacent to the nasopharyngeal mucosa posterior to the middle turbinate. Electrical impulses are applied through one or more electrodes in the stimulation device to the target nerve sufficient to modulate the nerve and treat the medical condition.

21 Claims, 11 Drawing Sheets

(56) References Cited

U.S. PATENT DOCUMENTS

| | | |
|---|---|---|
| 6,463,327 B1 | 10/2002 | Lurie et al. |
| 6,587,719 B1 | 7/2003 | Barrett et al. |
| 6,610,713 B2 | 8/2003 | Tracey |
| 7,797,041 B2 | 9/2010 | Libbus et al. |
| 2002/0099417 A1 | 7/2002 | Naritoku et al. |
| 2002/0183237 A1 | 12/2002 | Puskas |
| 2004/0243182 A1 | 12/2004 | Cohen et al. |
| 2004/0249416 A1 | 12/2004 | Yun et al. |
| 2005/0021092 A1 | 1/2005 | Yun et al. |
| 2005/0065574 A1 | 3/2005 | Rezai |
| 2005/0137644 A1 | 6/2005 | Boveja et al. |
| 2006/0074284 A1 | 4/2006 | Juola et al. |
| 2006/0100668 A1 | 5/2006 | Ben-David et al. |
| 2006/0100671 A1 | 5/2006 | Ridder |
| 2006/0173510 A1 | 8/2006 | Besio et al. |
| 2006/0178703 A1 | 8/2006 | Huston et al. |
| 2007/0027496 A1 | 2/2007 | Parnis et al. |
| 2007/0123952 A1 | 5/2007 | Strother et al. |
| 2007/0142886 A1 | 6/2007 | Fischell et al. |
| 2007/0150006 A1 | 6/2007 | Libbus et al. |
| 2007/0276449 A1 | 11/2007 | Gunter et al. |
| 2008/0021512 A1 | 1/2008 | Knudson et al. |
| 2008/0027513 A1 | 1/2008 | Carbunaru |
| 2008/0045776 A1 | 2/2008 | Fischell et al. |
| 2008/0132964 A1 | 6/2008 | Cohen et al. |
| 2008/0177190 A1 | 7/2008 | Libbus et al. |
| 2008/0208266 A1 | 8/2008 | Lesser et al. |
| 2008/0306325 A1 | 12/2008 | Burnett et al. |
| 2009/0157149 A1 | 6/2009 | Wahlgren et al. |
| 2009/0234419 A1 | 9/2009 | Maschino et al. |
| 2009/0287035 A1 | 11/2009 | Dietrich et al. |
| 2009/0299418 A1* | 12/2009 | Shalev et al. ............. 607/3 |
| 2010/0286553 A1 | 11/2010 | Feler et al. |
| 2011/0046432 A1 | 2/2011 | Simon et al. |
| 2011/0152967 A1 | 6/2011 | Simon et al. |
| 2011/0187534 A1* | 8/2011 | Cambre et al. ............ 340/572.8 |
| 2011/0213295 A1 | 9/2011 | Henley et al. |
| 2011/0224749 A1 | 9/2011 | Ben-David et al. |
| 2011/0230701 A1 | 9/2011 | Simon et al. |
| 2012/0029601 A1 | 2/2012 | Simon et al. |
| 2012/0071811 A1* | 3/2012 | Ansarinia ............... 604/20 |
| 2012/0283697 A1 | 11/2012 | Kim et al. |
| 2012/0303080 A1 | 11/2012 | Ben-David et al. |
| 2013/0218249 A1* | 8/2013 | Lamensdorf et al. ......... 607/118 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

* cited by examiner

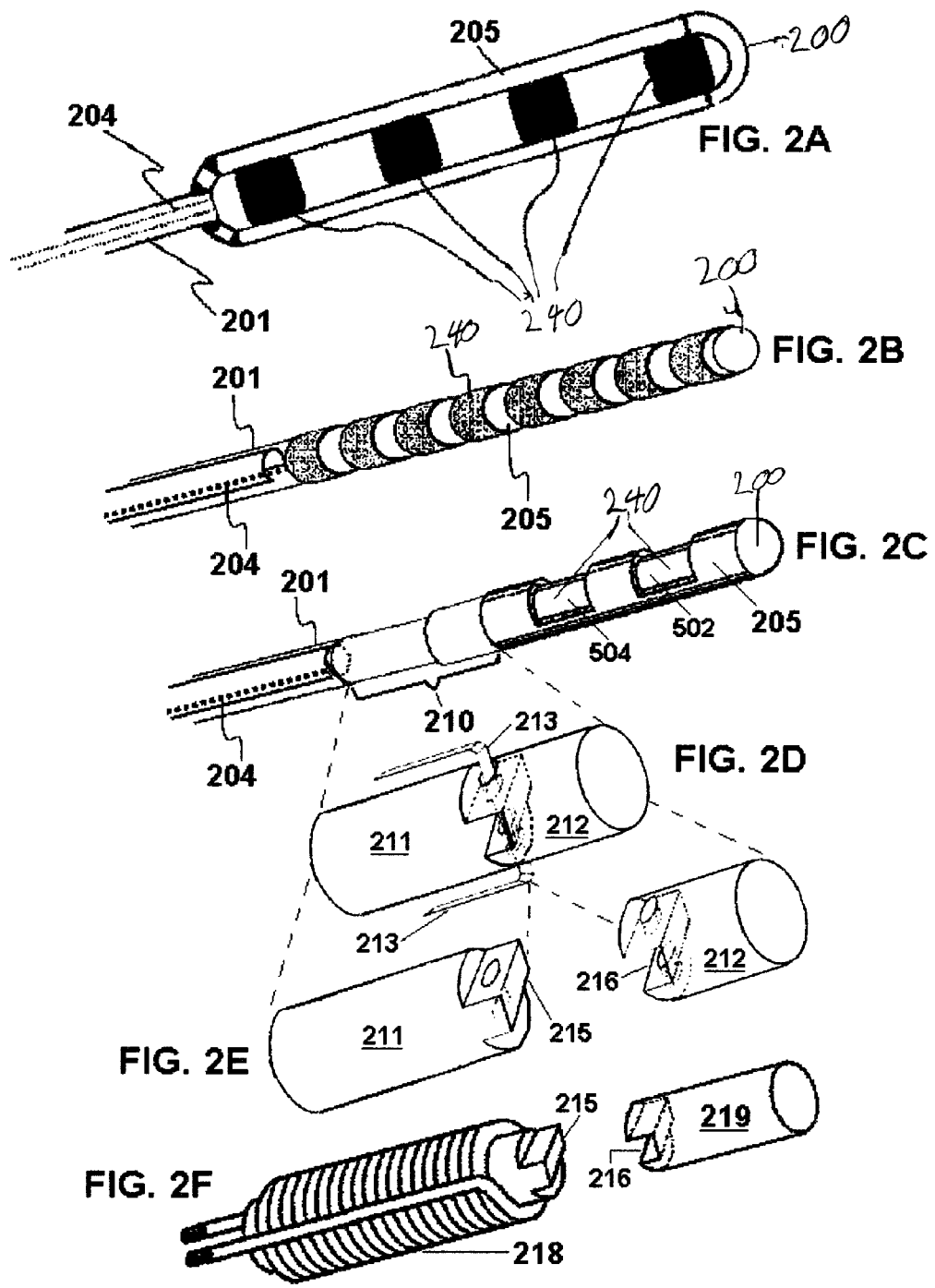

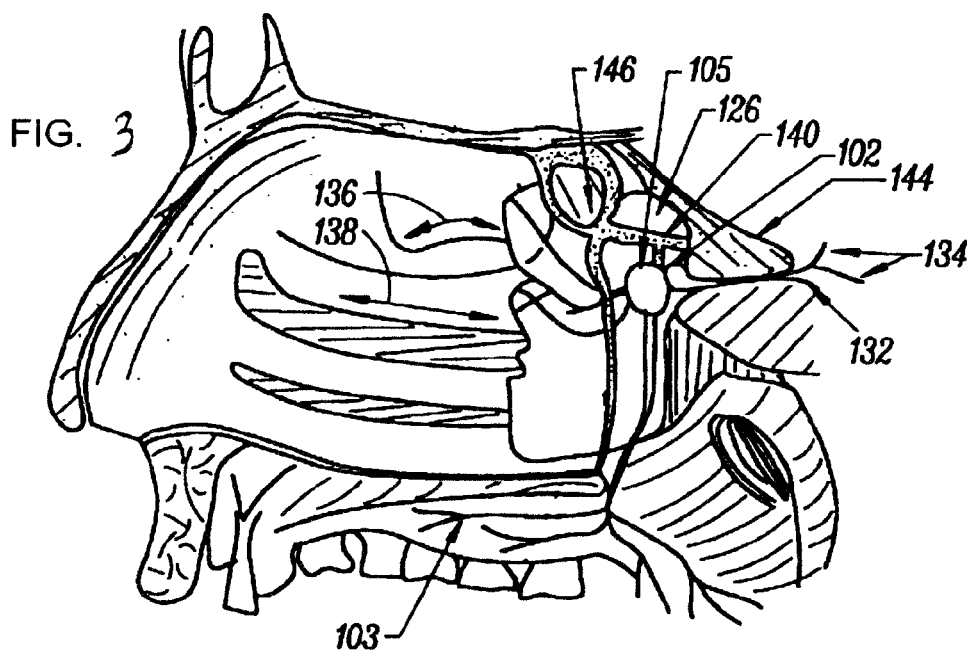

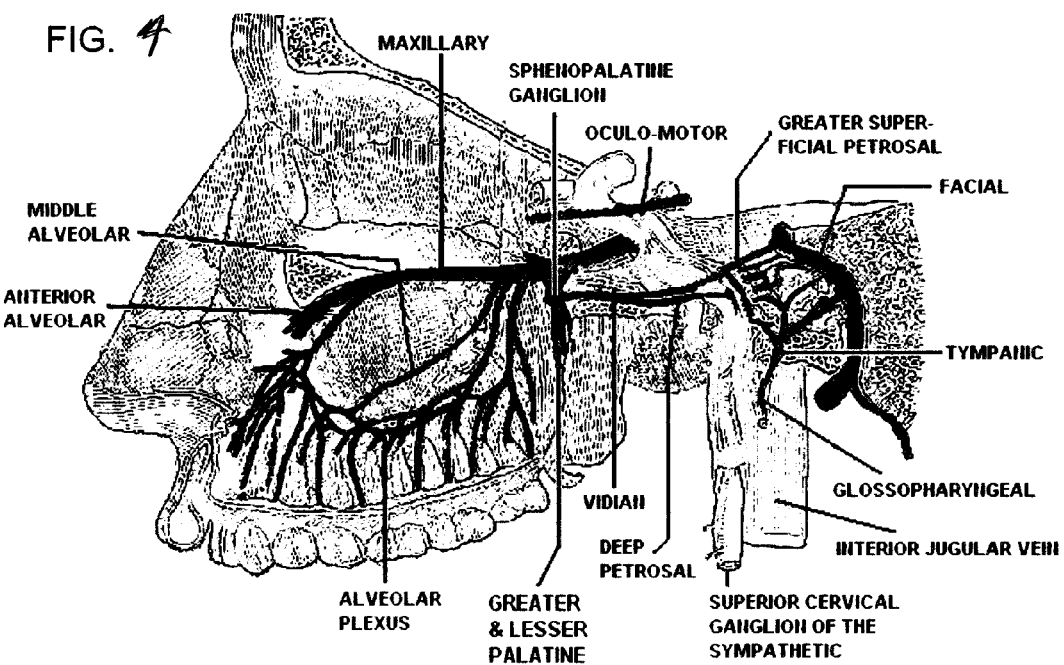

ADVANCEMENT PATH
THROUGH THE NOSTRIL

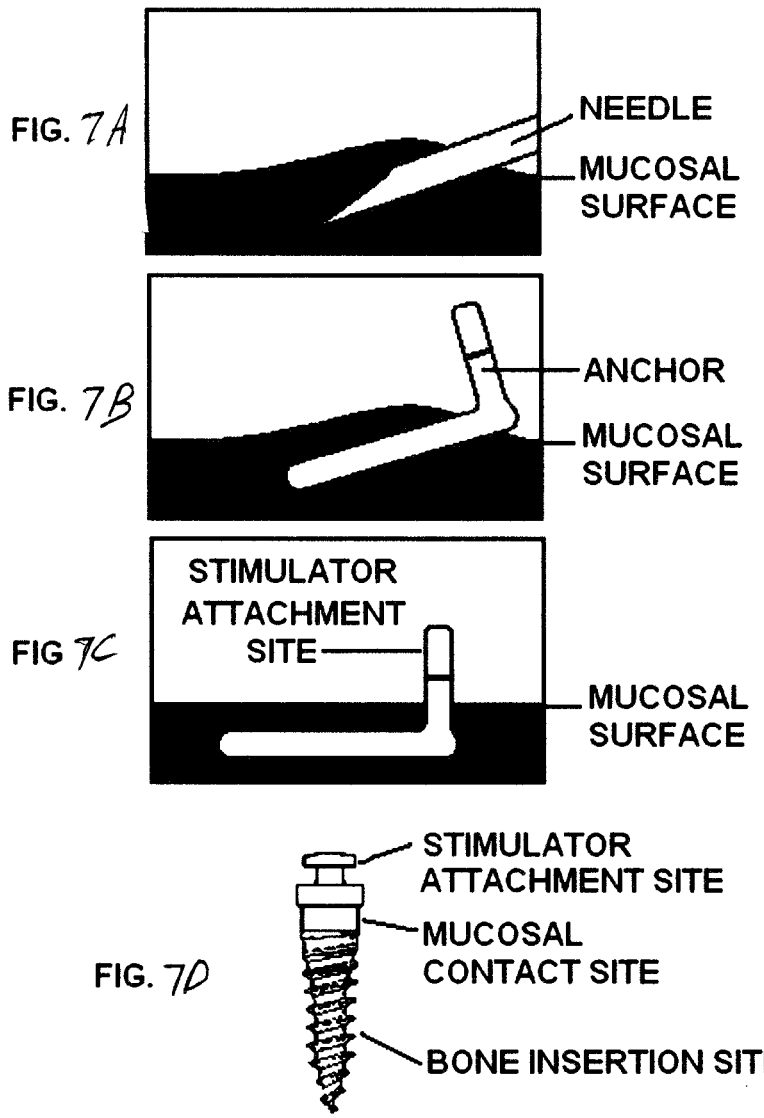

DIPOLE

HELIX

COIL

MEANDER

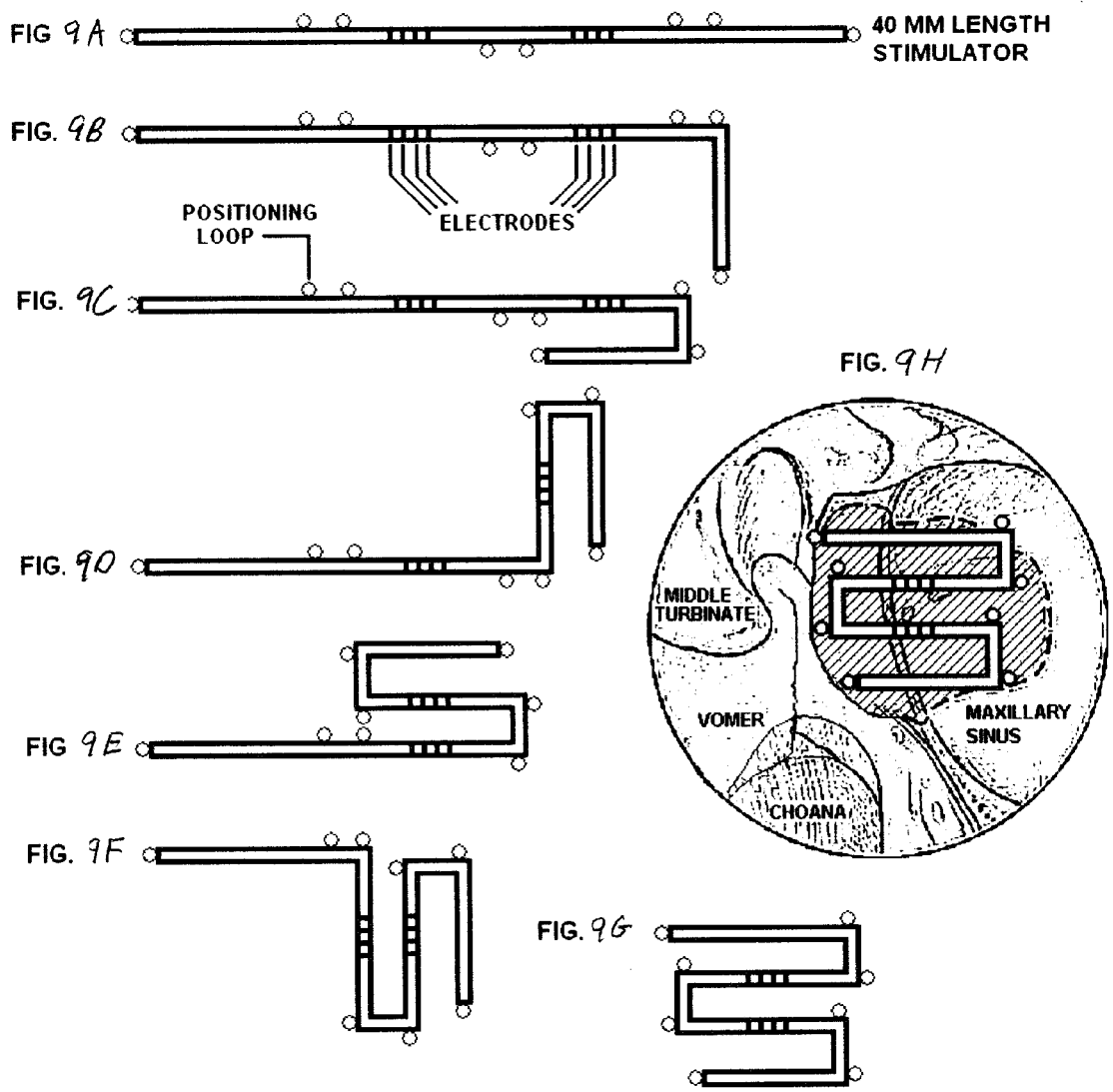

SYSTEMS AND METHODS FOR ELECTRICAL STIMULATION OF SPHENOPALATINE GANGLION AND OTHER BRANCHES OF CRANIAL NERVES

CROSS REFERENCE TO RELATED APPLICATIONS

The present application claims the benefit of U.S. Provisional Application Ser. No. 61/757,200 filed 27 Jan. 2013; which is incorporated herein by reference in its entirety.

BACKGROUND OF THE INVENTION

The field of the present invention relates to the delivery of energy impulses (and/or energy fields) to bodily tissues for therapeutic purposes. The invention relates more specifically to the use of electrical stimulation of the sphenopalatine ganglion (SPG) and other cranial nerves for treating disorders in a patient, such as primary headache.

The sphenopalatine ganglion (SPG) is a nerve ganglion found in the pterygopalatine (sphenopalatine) fossa, close to the sphenopalatine foramen (102 in FIG. 3; also known as the pterygopalatine ganglion, ganglion pterygopalatinum, Meckel's ganglion, and nasal ganglion). There are two SPG, on either side of the nose. The SPG is usually triangular or oblong, and in humans it is approximately 5 mm across its maximum extent. Its triangular shape reflects the three principal branches of the SPG: the vidian nerve superomedially, the branch from the maxillary nerve superolaterally, and the greater and lesser palatine nerves inferiorly. However, there is considerable SPG anatomical variation between individuals, and in some individuals, the SPG may not even exist as a single-unit structure [M. C. RUSU, F. Pop, G. C. Curca, L. Podoleanu, L. M. Voinea. The pterygopalatine ganglion in humans: A morphological study. Ann Anat 191 (2009):196-202].

The pterygopalatine fossa, within which the SPG is located, has the following boundaries: Anterior—the posterior wall of the maxillary sinus; Posterior—the medial plate of the pterygoid process; Medial—the perpendicular plate of the palatine bone; Superior—the sphenoid sinus; Lateral—communication with the infratemporal fossa; Superlateral—the maxillary branch of the trigeminal nerve exits the cranial vault through the foramen rotundum. The pterygopalatine fossa is approximately 1 cm wide and 2 cm high and can be viewed fluoroscopically as having the shape of a vase or pyramid on a lateral fluoroscopic view. Its neurovascular contents are complex, in which nerves and vessels of different individuals may occupy different locations within the fossa. Several surgical/anatomical routes have been described for reaching this fossa [Fabio ROBERT], Nicola Boari, Pietro Mortini, Anthony J. Caputy. The Pterygopalatine Fossa: An Anatomic Report. J Craniofac Surg 18(3,2007):586-590; Melissa McCarty STATHAM and Thomas A. Tami. Endoscopic anatomy of the pterygopalatine fossa. Operative Techniques in Otolaryngology—Head and Neck Surgery 17(3, 2006):197-200; LI, Jiping; Xu, Xiongwei; Wang, Jiadong; Jing, Xiaojie; Guo, Qinhua; Qiu, Yongming. Endoscopic Study for the Pterygopalatine Fossa Anatomy: Via the Middle Nasal Meatus-Sphenopalatine Foramen Approach. Journal of Craniofacial Surgery 20(3,2009):944-947; Christoph P. HOFSTETTER, Ameet Singh, Vijay K. Anand, Ashutosh Kacker and Theodore H. Schwartz. The endoscopic, endonasal, transmaxillary transpterygoid approach to the pterygopalatine fossa, infratemporal fossa, petrous apex, and the Meckel cave. J Neurosurg 113 (2010):967-974; FORTES F S, Sennes L U, Carrau R L, Brito R, Ribas G C, Yasuda A, Rodrigues A J Jr, Snyderman C H, Kassam A B. Endoscopic anatomy of the pterygopalatine fossa and the transpterygoid approach: development of a surgical instruction model. Laryngoscope 118(1,2008):44-49; ALFIERI A, Jho H D, Schettino R, Tschabitscher M. Endoscopic endonasal approach to the pterygopalatine fossa: anatomic study. Neurosurgery 52(2,2003):374-380; CAVALLO LM, Messina A, Gardner P, Esposito F, Kassam A B, Cappabianca P, de Divitiis E, Tschabitscher M. Extended endoscopic endonasal approach to the pterygopalatine fossa: anatomical study and clinical considerations. Neurosurg Focus 19(1,2005):E5, pp. 1-7; ISAACS SJ, Goyal P. Endoscopic anatomy of the pterygopalatine fossa. Am J Rhinol 21(5,2007):644-647].

Although it is primarily considered to be a parasympathetic ganglion, the SPG also conveys both sensory and sympathetic fibers which—unlike parasympathetic fibers—only pass through the ganglion without synapsing. The SPG is innervated by the greater pertrosal nerve (a branch of the facial nerve, i.e., the seventh cranial nerve) and has other important connections with the trigeminal nerve (fifth cranial nerve, particularly the maxillary nerve CN V2), internal carotid artery plexus of the sympathetic nervous system and, at least in animals, the anterior pituitary gland. Thus, the SPG has a complex center (see FIG. 2). It joins the maxillary branch of the trigeminal nerve via the pterygopalatine nerves. It joins the vidian nerve (nerve of the pterygoid canal), which is formed from the greater petrosal and deep petrosal nerves. It also connects with the greater and lesser palatine nerves which give rise to superior, posterior, lateral nasal, and pharyngeal nerves [M. C. RUSU and F. Pop. The anatomy of the sympathetic pathway through the pterygopalatine fossa in humans. Annals of Anatomy 192 (2010):17-22].

The SPG has been a clinical target to treat severe headaches since SLUDER first described the application of cocaine or alcohol to the vicinity of the SPG, by swabbing through the nostril to the nasopharyngeal mucosa posterior to the middle turbinate. This local anesthetic readily penetrates the mucosa to diffuse to the SPG. Later, SLUDER described the following injection into the pterygopalatine fossa with a silver nitrate solution and phenol, in order to inactivate the SPG chemically. A needle bent at a right angle 0.5 cm from its end is introduced along the septum of the nose to a point 0.33 cm posterior to and slightly above the posterior tip of the middle turbinate. Turning the needle outward brings it to the membrane covering the sphenopalatine foramen, puncturing the membrane, thereby bringing the tip of the needle into the pterygopalatine fossa. Alternatively, a straight 12 cm needle (with 1.2 mm diameter) may be used to reach the fossa. The inactivating chemical solutions were then injected into the pterygopalatine fossa [Greenfield SLUDER. Etiology, diagnosis, prognosis, and treatment of sphenopaltine ganglion neuralgia. Transactions of the American Medical Association. Section on Laryngology, Otology and Rhinology, 1913 Chicago: A.M.A. Press pp. 43-64].

Unfortunately, the SPG swabbing produces only a brief respite from pain, whether by using a cotton swab as originally described by SLUTER, or by means of a topical administration device [U.S. Pat. No. 8,231,588, entitled Methods for ameliorating pain and devices for delivering a medicament, to XIA]. In addition, injection into the pterygopalatine fossa is difficult to perform reliably due to considerable anatomical variability of the patients, with damage to the maxillary artery that lies next to the SPG being not uncommon. Furthermore, the nasal mucosa may slough during needle insertion. Nevertheless, such pharmacological blockade of the SPG has been claimed to be an effective treatment for headaches, asthma, angina, hiccups, epilepsy, glaucoma, neck pain, vascular spasms, facial neuralgias, blindness, low back pain, sciatica, ear ache, menstrual pain, temporomandibular joint dysfunction, and hyperthyroidism [Robert E. WINDSOR and Scott Jahnke. Sphenopalatine Ganglion Blockade: A Review and Proposed Modification of the Transnasal Technique. Pain Physician 7 (2004):283-286].

More recently, anesthetic has been injected into the pterygopalatine fossa using modifications of the Sluder methods and devices [Athma PRASANNA and P. S. N. Murthy. Sphenopalatine ganglion block under vision using rigid nasal sinuscope. Regional Anesthesia 18 (1993): 139-140; Ian Y. YANG and Saeed Oraee. A Novel Approach to Transnasal Sphenopalatine Ganglion Injection. Pain Physician 9 (2006):131-134; FELISATI G, Arnone F, Lozza P, Leone M, Curone M, Bussone G. Sphenopalatine endoscopic ganglion block: a revision of a traditional technique for cluster headache. Laryngoscope 116(8,2006):1447-1450]. Nevertheless, the internal maxillary artery may be at risk no matter where the pterygopalatine fossa is punctured [ISAACS SJ, Goyal P. Endoscopic anatomy of the pterygopalatine fossa. Am J Rhinol 21(5,2007):644-647].

In addition to the ganglion blockade using anesthetics that is described above, ablation (percutaneous radiofrequency, gamma knife, and surgical gangionectomy) and electrical nerve stimulation have been used to treat pain (especially cluster headaches) originating in, or emanating from, the SPG. The objective of the ablation is to irreversibly damage the SPG to such an extent that it cannot generate the nerve signals that cause pain. This is not a preferred method because ablation would destroy useful neurophysiological functions of the SPG, notwithstanding the pain that the SPG may cause.

In contrast to ablation, the objective of electrical nerve stimulation is to reversibly damage or otherwise inhibit or block activity the SPG. A significant advantage of electrical stimulation over ablation is that it is a reversible procedure. In that regard, SPG neurostimulation resembles the stimulation of other nerves for the treatment of primary headache disorders [Brian JENKINS Stewart J. Tepper. Neurostimulation for Primary Headache Disorders, Part 1: Pathophysiology and Anatomy, History of Neuromodulation in Headache Treatment, and Review of Peripheral Neuromodulation in Primary Headaches. Headache 51 (2011):1254-1266; Brian JENKINS Stewart J. Tepper. Neurostimulation for Primary Headache Disorders: Part 2, Review of Central Neurostimulators for Primary Headache, Overall Therapeutic Efficacy, Safety, Cost, Patient Selection, and Future Research in Headache Neuromodulation. Headache 51 (2011):1408-1418].

There are several anatomical approaches to the SPG, comprising: 1) a transnasal route as described above; 2) a transoral approach with a dental needle up to the sphenopalatine foramen through the posterior palatine canal and; 3) a lateral approach with a straight needle to the pterygopalatine fossa through the infratemporal fossa; 4) an infrazygomatic approach, in which the skin entry is at a site overlying the pterygopalatine fossa, just inferior to the zygoma and anterior to the mandible. DuPLESSIS describes other routes through the mouth and outer skin of the face [M. DuPLESSIS, N. Naysa, M. C. Bosman. Preliminary results on a study to locate the pterygopalatine fossa using mathematical formulae. Clinical Anatomy 23(8,2010):931-935; Micah HILL, Rakesh K. Chandra, Robert C. Kern. Approaches to the pterygopalatine space—Caldwell-Luc and beyond. Operative Techniques in Otolaryngology 21 (2010):117-121; SYED M. I. and Shaikh A. Radiology of Non-Spinal Pain Procedures. A Guide for the Interventionist. Chapter 2. Head and Neck. pp. 5-42. Heidelberg: Springer, 2011].

Until the present invention, neither radiofrequency ablation nor electrical stimulation of the SPG has been disclosed using a transnasal route. Avoidance of the transnasal route has apparently been due to the fact that surgical access to the pterygopalatine fossa through the nose is considered difficult, because of the protected position of the fossa and because of its complex and somewhat variable neurovascular anatomy. Avoidance of a transnasal route has also been due to structural and energizing limitations of prior electrical stimulators, which would make their introduction through the nose essentially impossible.

Thus, all ablation and electrical stimulation methods to date have approached the SPG only via the transoral or infrazygomatic approaches. Investigators using ablation described use of the infrazygomatic approach [NAROUZE S, Kapural L, Casanova J, Mekhail N. Sphenopalatine ganglion radiofrequency ablation for the management of chronic cluster headache. Headache 49(4,2009):571-577; NAROUZE SN. Role of sphenopalatine ganglion neuroablation in the management of cluster headache. Curr Pain Headache Rep 14(2, 2010):160-63].

When implanting an SPG electrical stimulator, IBARRA also used the infrazygomatic route, as did TEPPER and ANSARINIA. [IBARRA E. Neuromodulación del Ganglio Esfenopalatino para Aliviar los Síntomas de la Cefalea en Racimos. Reporte de un Caso. Boletín E I Dolor 46(16,2007): 12-18; Stewart J. TEPPER; Ali Rezai, Samer Narouze, Charles Steiner, Pouya Mohajer, Mehdi Ansarinia. Acute Treatment of Intractable Migraine With Sphenopalatine Ganglion Electrical Stimulation. Headache 49 (2009):983-989; Mehdi ANSARINIA, Ali Rezai, Stewart J. Tepper, Charles P. Steiner, Jenna Stump, Michael Stanton-Hicks, Andre Machado, Samer Narouze. Electrical Stimulation of Sphenopalatine Ganglion for Acute Treatment of Cluster Headaches. Headache 50 (2010):1164-1174; U.S. Pat. No. 6,526,318, entitled Stimulation method for the sphenopalatine ganglia, sphenopalatine nerve, or vidian nerve for treatment of medical conditions, to ANSARINIA].

On the other hand, SCHOENEN, PAPAY, and SHALEV used the transoral approach for electrical stimulation of the SPG [Jean SCHOENEN, Rigmor Højland Jensen, Michel Lanteri-Minet, Miguel J A Lainez, Charly Gaul, Amy M Goodman, Anthony Caparso and Arne May. Stimulation of the sphenopalatine ganglion (SPG) for cluster headache treatment. Pathway CH-1: A randomized, sham-controlled study. Cephalalgia. 2013 Jan. 11, pp. 1-15 [Epub ahead of print]; Application US20120209286, entitled Surgical guide and method for guiding a therapy delivery device into the pterygopalatine fossa, to PAPAY et al; Application US20110160623, entitled External stimulation of the SPG, to SHALEV; US20060195169, entitled Surgical tools and techniques for stimulation, to GROSS et al.; US20080172102, entitled Transmucosal electrical stimulation, to SHALEV].

SUMMARY OF THE INVENTION

The present invention is concerned with devices and methods for the treatment of a medical condition of a patient, in which the treatment involves the electrical stimulation of a selected nerve. In particular, the devices and method of the present invention use electrical stimulation to reversibly inhibit or block activity of the SPG or other branches of cranial nerves.

In one aspect of the invention, a method for treating a patient with a disorder, such as primary headache, comprises advanced an electrode lead or leads transnasally to a target site at or adjacent to a nerve within the patient. In preferred embodiment, the electrode lead(s) are delivered through one or both nostrils of the patient to the nasopharyngeal mucosa posterior to the middle turbinate adjacent to the SPG. The present invention differs from the prior art in that the disclosed electrical stimulator is intended for convenient and rapid transnasal placement in the vicinity of the SPG. The stimulation may be used to treat any condition that has been treated by anesthetic blockade of the SPG, particularly cluster headache. Unlike the previously described SPG electrical stimulators, the present stimulator may be used essentially noninvasively, thus avoiding any potential damage to the pterygopalatine fossa.

In one embodiment, a stimulation device comprises one or more electrodes and a pulse generator and is configured for implantation at a target site adjacent to or near excitable tissue, such as the SPG, within the patient's body. In certain embodiments, the power source may also be implanted with the stimulation device or at another location within the patient's body. In other embodiments, the energy that is used to produce the impulses is received wirelessly by a dipole or other type of antenna that is also part of the stimulator. The received energy is preferably from far-field or approximately plane wave electromagnetic waves in the frequency range of about 0.3 to 10 GHz, more preferably about 800 MHz to 6 GHz and even more preferably about 800 MHz to 1.2 GHz. In an exemplary embodiment, the carrier signal is around 915 MHz. The electrical energy is transmitted from the antenna of an external energy source that is preferably a meter or more outside the patient, but that may also be situated closer or even be placed within the patient. In some embodiments, the transmitter may be worn around the neck as a pendant, placed in a pocket, attached to a belt or watch, or clipped to clothing.

In another aspect of the invention, the stimulator circuit comprises either a battery or a storage device, such as a capacitor, for storing energy or charge and then delivering that charge to the circuit to enable the circuit to generate the electrical impulses and deliver those impulses to the electrodes. The energy for the storage device is preferably wirelessly transmitted to the stimulator circuit through a carrier signal from the external controller. In the preferred embodiments, the energy is delivered to the energy storage device between electrical impulses. Thus, the energy is not being delivered in "real-time", but during the periods when the pulse is not being delivered to the nerve or during the refractory period of the nerve.

The electrical impulse is sufficient to modulate a selected nerve (e.g., SPG) at or near the target region to treat a condition or symptom of the patient. The stimulator is configured to induce a peak pulse voltage sufficient to produce an electric field in the vicinity of the nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and/or an electrical field gradient of greater than 2 V/m/mm.

In another aspect of the invention, the stimulation device is positioned adjacent to or near the mucosa area posterior to the middle turbinate and secured to the mucosal surface with, for example, medical glue, dental adhesives or the like. A surgical net may be placed over the stimulation device to help keep it in place. Alternatively, the stimulation device may be attached to the underlying tissue using sutures that are placed through loops that are attached to the stimulator. A significant advantage of this method is that there is no risk of damaging the blood vessels and nervous tissue within the pterygopalatine (sphenopalatine) fossa, because the fossa is not breached.

Once the stimulation device is in position at the target site, energy is transmitted to the device from an external power source. One or more electrical impulses are generated and applied to the target nerve to modulate that nerve and treat the patient's condition.

In another embodiment of the present invention, one or more anchors are placed under the mucosa, with a portion of the anchor(s) extending through the mucosa. The electrode leads are then attached to this portion of the anchor(s) outside of the pterygopalatine (sphenopalatine) fossa. Alternatively, the electrode leads may comprise one or more barbs held to the mucosa by inserting the barb through the mucosa.

In another embodiment, one or more anchors are placed into a rigid structure within the patient, such as the pterygoid process or the vomer. The electrode leads are then attached to the anchor(s) outside of the pterygopalatine (sphenopalatine) fossa.

In yet another embodiment, a needle is inserted through the mucosa into the pterygopalatine (sphenopalatine) fossa, at a target site adjacent to or near a blood vessel or nerve. A lead blank is then inserted into the lumen of the needle and advanced along a path of least resistance, e.g., through fat tissue, such that the lead blank is deflected from the more solid nerve and blood vessel tissue as it advances. The lead blank creates a path through the tissue. The lead blank is then withdrawn from the needle, and an electrode lead is advanced into the fossa through the lumen of the needle, taking the safe path generated by the lead bank. The stimulator may be pushed entirely into the fossa, using a pushwire behind it in the needle, or a portion of the stimulator may remain outside of the fossa. In either case, the needle is withdrawn, and the site of needle insertion is sealed with surgical glue (also around the stimulator if it protrudes through the mucosa).

In yet another embodiment, a flap is made in the mucosa to expose the SPG. The electrode lead is then positioned at a selected location within the fossa adjacent to or near the SPG. The electrode lead is secured to the fossa, e.g., with surgical glue, sutures or the like. The surgical flap is then closed and sealed. As in the previous embodiment, the stimulator may be situated entirely within the fossa, or a portion of the electrode may be left protruding through the sealed mucosa.

The system may also comprise a docking station that is used to charge a rechargeable battery within the stimulation device or the power source. The docking station and stimulation device may also transmit data to one another. They may also transmit data to, and receive data from, a computer program in a patient interface device, such as a mobile phone or nearby computer. Physiological sensors may transmit their signals to the stimulation device, docking station, and/or interface device. Such data transmission is preferably wireless, but wired communication between devices is also contemplated.

The novel systems, devices and methods for treating medical conditions are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

This application refers to the following patents and patent applications, the entire disclosures of which are hereby incorporated here by reference for all purposes: U.S. patent application Ser. No. 13/279,437 filed Oct. 24, 2011, U.S. patent application Ser. No. 13/222,087 filed Aug. 31, 2011, U.S. patent application Ser. No. 13/183,765 filed Jul. 15, 2011, U.S. patent application Ser. No. 13/183,721 filed Jul. 15, 2011, U.S. patent application Ser. No. 13/109,250 filed May 17, 2011, U.S. patent application Ser. No. 13/075,746 filed Mar. 30, 2011, U.S. patent application Ser. No. 13/005,005 filed Jan. 12, 2011, U.S. patent application Ser. No. 12/964,050 filed Dec. 9, 2010, U.S. patent application Ser. No. 12/859,568 filed Aug. 9, 2010, U.S. patent application Ser. No. 12/408,131 filed Mar. 20, 2009, U.S. patent application Ser. No. 12/612,177 filed Nov. 9, 2009 now U.S. Pat. No. 8,041,428 issued Oct. 18, 2011, U.S. patent application Ser. No. 12/859,568, filed Aug. 19, 2010, U.S. patent application Ser. No. 13/208,425, filed Aug. 12, 2011, U.S. patent application Ser. No. 12/964,050, filed Dec. 9, 2010, U.S. patent application Ser. No. 13/005,005, filed Jan. 12, 2011, U.S. application Ser. No. 13/024,727, filed Feb. 10, 2011, U.S. application Ser. No. 13/075,746, filed Mar. 30, 2011, U.S. application Ser. No. 13/109,250, filed May 17, 2011, U.S. application Ser. No. 13/183,721, filed Jul. 15, 2011, U.S. application Ser. No. 13/222,087, filed Aug. 31, 2011, U.S. application Ser. No. 13/357,010, filed Jan. 24, 2012, U.S. application Ser. No. 13/736,096, filed Jan. 8, 2013, U.S. application Ser. No. 13/603,781, filed Sep. 5, 2012, U.S. application Ser. No. 13/671,859, filed Nov. 8, 2012, U.S. application Ser. No. 13/731,035, filed Dec. 30, 2012, U.S. application Ser. No. 13/858,114, filed Apr. 8, 2013 and U.S. application Ser. No. 13/872,116, filed Apr. 29, 2013 and U.S. application Serial No. 14/071,577, titled Nerve Stimulator System and filed Nov. 4, 2013.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 2A illustrates one embodiment of an electrode assembly in an implantable stimulation device according to the present invention;

FIG. 2B-2F illustrate additional embodiments of electrode assemblies according to the present invention.

FIG. 3 is a cross-sectional view of the nasal cavities;

FIG. 4 illustrates some of the nerves in and around the nasal cavities;

FIGS. 7A-7D illustrate various methods of securing the stimulation device to the target site according to the present invention;

FIGS. 9A-9G illustrate various electrode configurations within the stimulation device of the invention;

FIG. 9H illustrates an electrode configuration sutured in an anatomical location in accordance with the present invention.

DETAILED DESCRIPTION OF THE PREFERRED EMBODIMENTS

Figure 1A:
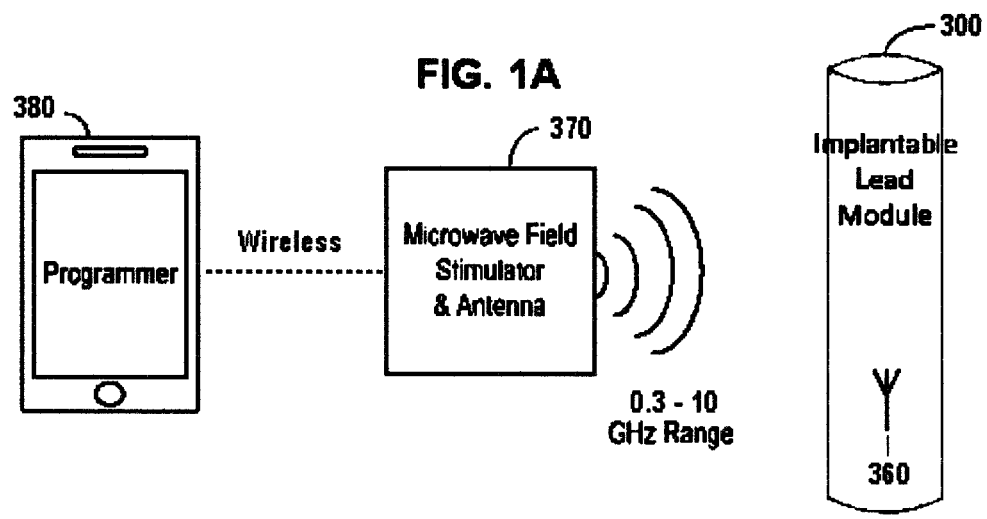
FIG. 1A is a schematic view of a nerve modulating system (implantable lead module or electrical stimulator) according to one or more aspects of the present invention.

The present invention is concerned with devices and methods for the treatment of a medical condition of a patient, in which the treatment involves the electrical stimulation of a selected nerve. In particular, the devices and method of the present invention use electrical stimulation to modulate, stimulate, reversibly inhibit and/or block activity of the SPG or other branches of cranial nerves.

In one aspect of the invention, a method for treating a patient with a disorder, such as primary headache, comprises advancing an electrode lead or leads transnasally to a target site at or adjacent to a nerve within the patient. In preferred embodiments, the electrode lead(s) are delivered through one or both nostrils of the patient to the nasopharyngeal mucosa posterior to the middle turbinate adjacent to the SPG. The present invention differs from the prior art in that the disclosed electrical stimulator is intended for convenient and rapid transnasal placement in the vicinity of the SPG. The stimulation may be used to treat any condition that has been treated by anesthetic blockade of the SPG, particularly cluster headache. Unlike the previously described SPG electrical stimulators, the present stimulator may be used essentially noninvasively, thus avoiding any potential damage to the pterygopalatine fossa. The present stimulator may also be used invasively, and it may also be placed transnasally in the vicinity of other branches of cranial nerves. Electrical waveforms for use with the stimulator are disclosed that may be used to preferentially block or otherwise modulate the activity of particular nerves in and around the SPG.

In one embodiment, a stimulation device comprises one or more electrodes and a pulse generator and is configured for implantation at a target site adjacent to or near excitable tissue, such as the SPG, within the patient's body. In certain embodiments, the power source may also be implanted with the stimulation device or at another location within the patient's body. In other embodiments, the energy that is used to produce the electrical impulses is received wirelessly by a dipole or other type of antenna that is also part of the stimulator. In other embodiments, the stimulation device may be placed at the target site without implantation and directly coupled with wires to the power source. In these embodiments, electrical connection wires may extend from the power source (which may be external to the patient) through one of the patient's nostrils to the stimulation device.

FIG. 3 is a cross-sectional view illustrating some of the important structures of the nose and nasal cavities. As shown, the maxilla 103 reside underneath the superior nasal turbinate 136, middle nasal turbinate 138 and sphenoid sinus 145. Posterior to the sphenoid sinus 145 is the sphenopalatine nerve (SPN) 105, sphenopalatine fossa 126, maxillary nerve 140 and the sphenopalatine ganglion (SPG) 102. Posterior to those structures are the petrous bone 144, deep and greater petrosal nerves 134 and the vidian nerve VN 132.

Figure 5:
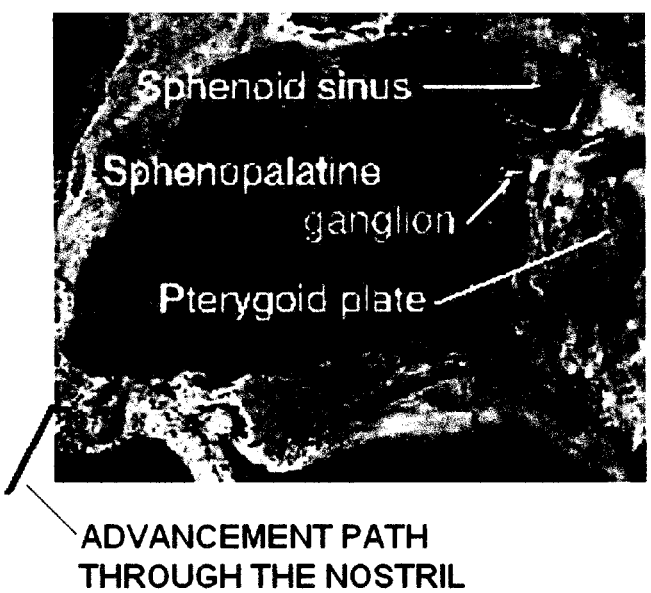
FIG. 5 illustrates an advancement path for an electrode lead or stimulation device through the nostril of a patient according to the present invention.

As shown in the sagittal section through the nasal cavity and sphenoid sinus in FIG. 5, the stimulator is advanced on a path through the nostril and along the superior border of the middle turbinate, until it reaches the posterior wall of the nasopharynx in the vicinity of the SPG. A curved path as shown may be used, and a straight path is also possible.

Figure 6A:
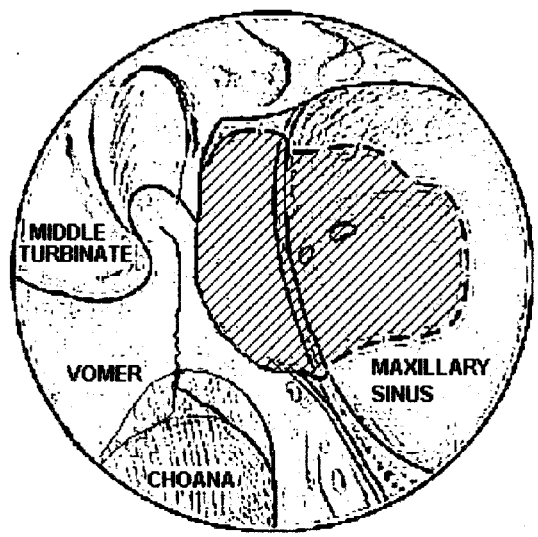
FIGS. 6A and 6B illustrate target areas for positioning the stimulation device of the present invention.
Figure 6B:
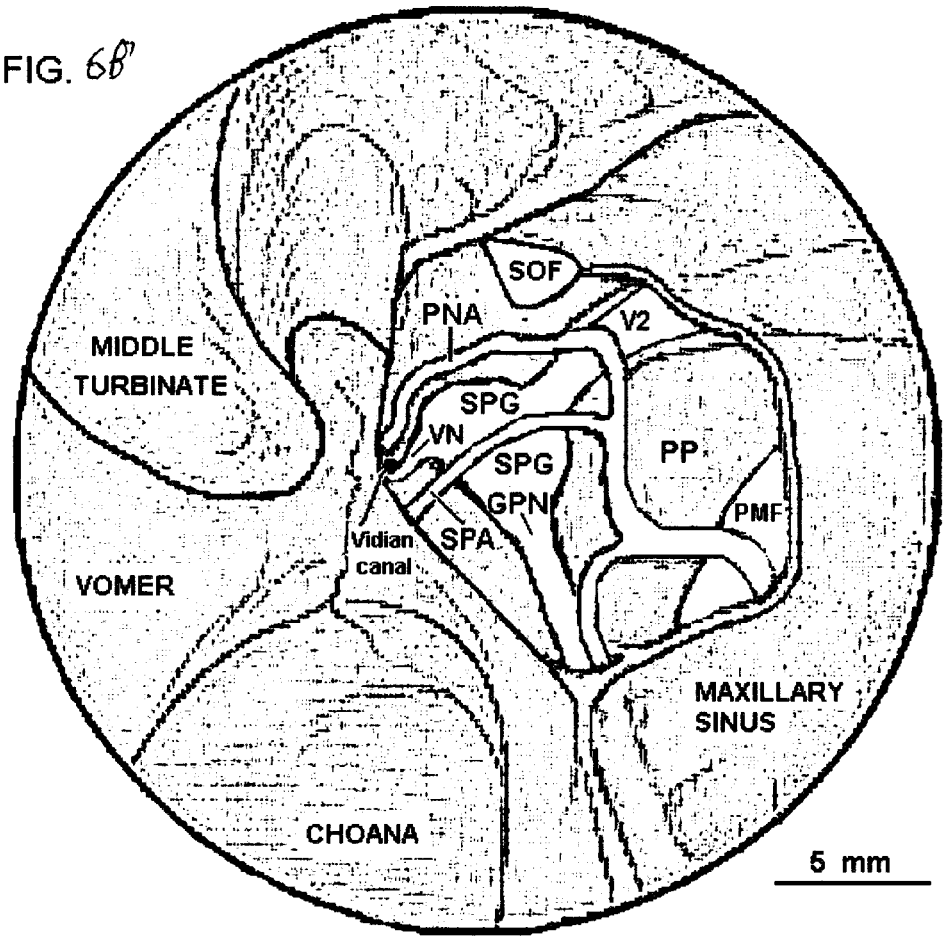

At the end of the path, the nasopharyngeal mucosa posterior to the middle turbinate will appear through an endoscope as shown in FIG. 6A [Melissa McCarty STATHAM and Thomas A. Tami. Endoscopic anatomy of the pterygopalatine fossa. Operative Techniques in Otolaryngology—Head and Neck Surgery 17(3,2006):197-200]. The SPG lies a few millimeters under the mucosa area shown by hash marks (//////) in FIG. 6A. If an antrostomic flap is cut in the mucosa along the margins of the area shown by hash marks in FIG. 6A and folded back, the objects shown in the enlarged FIG. 6B may be observed, provided that a substantial amount of fat is first removed. Thus, when the flap is first folded back, only the blood vessels identified as the posterior nasal nerve (PNA) and sphenopalatine artery (SPA) would be observed to be situated in fatty tissue. It may be possible to visualize the SPG by carefully lifting the fat tissue, or alternatively by removing it layer by layer. In either case, care must be taken to avoid damaging the blood vessels and nervous tissue. The objective then is to electrically stimulate the SPG, with or without physical exposure of the SPG. Other items labeled in FIG. 6B are as follows: vidian nerve (VN), maxillary division of the trigeminal nerve (V2), greater palatine nerve (GPN), pterygomaxillary fissure (PMF), pterygoid process (PP), and superior orbital fissure (SOF).

The present invention discloses five methods for placing the stimulator in the vicinity of the SPG. With three of the methods, the electrode remains largely outside of the pterygopalatine (sphenopalatine) fossa, so that the stimulation is effectively noninvasive. With the other two methods, the stimulator is placed within the pterygopalatine (sphenopalatine) fossa.

In the first embodiment, the stimulator is placed atop the mucosa area shown by hash marks in FIG. 6A, and medical glue such as cyanoacrylates or even denture adhesives are used to secure the stimulator to the mucosal surface. A surgical net may be placed over the stimulator to help keep it in place. Alternatively, the stimulator is attached to the underlying tissue using sutures that are placed through loops that are attached to the stimulator. This first, essentially noninvasive, embodiment might in some cases be considered to be temporary. When used temporarily, it may be used to determine whether the electrical stimulation will be effective, before using a more invasive approach. A significant advantage of this method is that there is no risk of damaging the blood vessels and nervous tissue within the pterygopalatine (sphenopalatine) fossa, because the fossa is not breached. Another advantage is its relative technical simplicity.

In the second embodiment (submucosal anchoring), one or more anchors are placed under the mucosa, with a portion of the anchor extending through the mucosa to attach the stimulator outside the pterygopalatine (sphenopalatine) fossa. FIG. 7A shows a needle being used to prepare the site of insertion of the anchor. FIG. 7B shows the anchor being inserted into that site. FIG. 7C shows the final position of the anchor, along with the location of the site of stimulator attachment outside the pterygopalatine (sphenopalatine) fossa. Alternatively, the stimulator may have one or more barbs at its ends, and the stimulator is held to the mucosa by inserting the barb through the mucosa.

The third embodiment is like the second, except that the anchor is inserted more permanently into a rigid structure such as the pterygoid process (PP in FIG. 6B) or the vomer. An example of such an anchor is shown in FIG. 7D. The stimulator is then attached to the anchor outside of the pterygopalatine (sphenopalatine) fossa at the site of attachment shown in FIG. 7D. Thus, the stimulator in the first three embodiments lies mostly outside the fossa.

In the fourth embodiment, a needle is inserted through the mucosa by approximately 1 mm, into the pterygopalatine (sphenopalatine) fossa, at a site that is unlikely to encounter blood vessels or nerves. The site may have been selected by using high resolution MR imaging of the contents of the fossa, ultrasound imaging with a transducer at the tip of a catheter inserted through the nostril, or by the statistical likelihood of a safe insertion at some site. A lead blank (e.g., teflon coated flexible wire, possibly with a spatula-shaped end) is then inserted into the lumen of the needle. The lead blank is advanced along a path of least resistance, e.g., through fat tissue, but being deflected from the more solid nerve and blood vessel tissue as it advances. Thus, the path that the lead blank takes is not necessarily known in advance, but instead opens a safe wormhole within the fossa. The lead blank is then withdrawn from the needle, and a catheter-like stimulator is advanced into the fossa through the lumen of the needle, taking the safe path that the lead blank had made. The stimulator may be pushed entirely into the fossa, using a pushwire behind it in the needle, or a portion of the stimulator may remain outside of the fossa. In either case, the needle is withdrawn, and the site of needle insertion is sealed with surgical glue (also around the stimulator if it protrudes through the mucosa).

In the fifth embodiment, a flap is made in the mucosa, and the SPG is surgically exposed as shown in FIG. 6B. Alternatively, any other surgical method of safely entering the fossa may be used. The stimulator is then placed at a selected location within the fossa. It may be held in place using surgical glue or by placing sutures through loops that are attached to the stimulator. The surgical flap is then closed and sealed with surgical glue. As in the previous embodiment, the stimulator may be situated entirely within the fossa, or a portion of the electrode may be left protruding through the sealed mucosa.

Description of the Nerve Stimulating/Modulating Devices

Figure 1B:
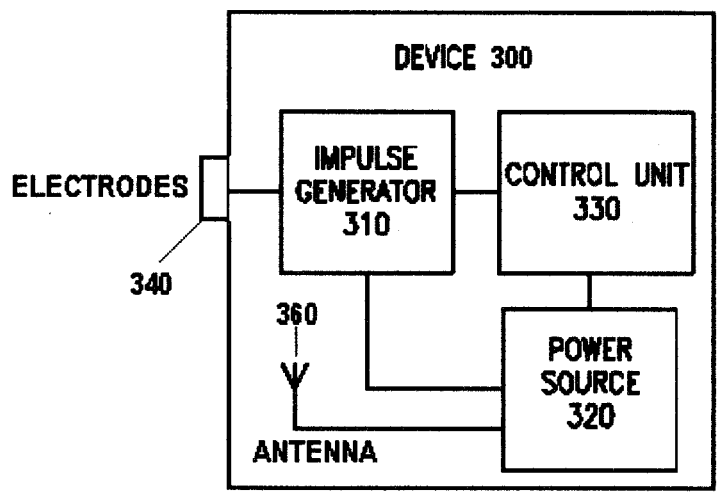
FIG. 1B is a schematic view of an implantable stimulation device according to the present invention.
Figure 1C:
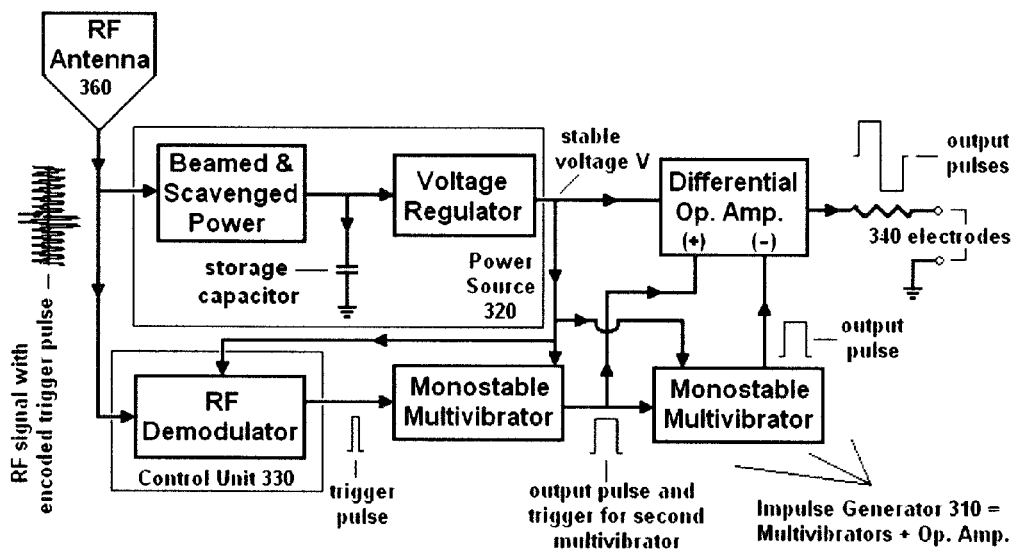
FIG. 1C is a more specific view of the components of one embodiment of the implantable stimulation device of FIG. 1B

FIGS. 1A-1C illustrate one embodiment of a nerve modulating device 300 of the present invention (also known as an implantable lead module or simply an electrical nerve stimulator). Nerve modulating device 300 is preferably powered by the receipt of far-field or approximately plane wave electromagnetic energy with frequencies in the range of 0.3 to 10 GHz (preferably about 800 MHz to about 6 GHz, and more preferably about 800 MHz to about 1.2 MHz) which is received wirelessly by an antenna 360 within, or attached to, the device 300. The energy that powers the nerve modulating device 300 is transmitted by an external device, which in FIG. 1A is labeled as a Controller 370. Controller 370 is in turn controlled by a programmer device 380, which preferably communicates with controller 370 wirelessly. In operation, the nerve modulating device 300 is implanted within the patient, the controller 370 may be either outside of the patient or implanted within the patient, and the programmer 380 is operated manually by the patient or a caregiver. The antenna of the controller 370 is actively tuned/matched to the resonant frequency of an antenna in the implanted device 300 so that the maximum efficiency of power transmission is achieved. There may be several antennae at various orientations in the external unit and/or in the implanted signal generator to enhance coupling efficiency in various orientations. The unit 370 supplying power and control to the implanted device 300 could be AC powered and/or battery powered. If powered by rechargeable batteries, a battery charger may be an accessory to the system. The controller 370 is preferably both portable and rechargeable. In one embodiment, it may be worn around the neck as a pendant, placed in a pocket, or clipped to clothing. This wireless transmitter 370 is preferably recharged at a recharging base and has a significant range of transmission, preferably up to four feet, so that patients can sleep without having to wear the transmitter.

FIG. 1B is a more detailed schematic diagram of the nerve modulating device 300 for delivering electrical impulses to nerves. As shown, device 300 comprises an electrical impulse generator 310; a power source 320 coupled to the electrical impulse generator 310; a control unit 330 in communication with the electrical impulse generator 310 and coupled to the power source 320; and one or more electrodes 340 coupled to the electrical impulse generator 310. Nerve modulating device 300 is configured to generate electrical impulses sufficient to modulate the activity of one or more selected regions of a nerve (not shown). The power source 320 receives energy wirelessly via an antenna 360, wherein the energy is in the form of far-field or approximately plane-wave electromagnetic waves with frequencies in the range of 0.3 to 10 GHz, preferably about 800 MHz to about 1.2 MHz.

The control unit 330 may control the electrical impulse generator 310 for generation of a signal suitable for amelioration of a patient's condition when the signal is applied via the electrodes 340 to the nerve. It is noted that nerve modulating device 300 excluding the electrodes 340 may be referred to by its function as a pulse generator. U.S. Patent Application Publications 2005/0075701 and 2005/0075702, both to SHAFER, both of which are incorporated herein by reference, relating to stimulation of neurons of the sympathetic nervous system to attenuate an immune response, contain descriptions of pulse generators that may be applicable to various embodiments of the present invention.

FIG. 1C illustrates one embodiment of the nerve modulating device 300 that consumes relatively little power and may therefore receive power from a correspondingly weak and/or distant external transmitter. To achieve low power consumption, the embodiment is designed to use a minimum of components. This may be accomplished by designing the device to produce constant voltage pulses, rather than constant current pulses, because circuits for the latter are more complex and consume more power than the former. However, for some patients a constant current pulse may be preferred, depending on the detailed anatomy of the patient's neck in the vicinity of the stimulated nerve (see below). Consequently, constant current pulses are also contemplated by the invention [DELIMA, J. A. and Cordeiro, A. S. A simple constant-current neural stimulator with accurate pulse-amplitude control. Engineering in Medicine and Biology Society, 2001. Proceedings of the 23rd Annual International Conference of the IEEE (Vol. 2, 2001) 1328-1331]. In either case, simplicity of circuit design is provided by a design that makes the amplitude of the pulse constant, rather than by allowing the amplitude to be variable. Accordingly, the present invention modulates the stimulation power to the nerve by altering the number and timing of the pulses, rather than by modulating the amplitude of individual pulses. Additional simplicity of design may be achieved by using communication that occurs in one direction only, from the transmitter to the stimulator (simplex communication according to the ANSI definition, rather than half or full duplex communication).

The stimulator circuit is novel in that it removes one (or more) elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of pulses, but by then controlling the number and timing of pulses that the nerve experiences, in order to achieve the same physiologically desirable level of ner'[ ]=-ve stimulation. In essence, this invention uses an adjustable number of fixed voltage (or fixed current) pulses with fixed duration to elicit desired changes in nerve response. These fixed voltage pulses create one long continuous pulse to the nerve to ensure that sufficient energy is delivered to the nerve to cause the nerve to reach its action potential and fire. Thus, the present invention reaches the threshold energy level for a nerve to fire by adjusting the duration of the pulse received by the nerve, rather than adjusting the amplitude of the pulse.

In another aspect of the invention, the specific number of fixed amplitude pulses that will be delivered to the nerve is preferably determined through an iterative process with each patient. Once the surgeon determines the number of fixed voltage pulses required to stimulate the nerve for a particular patient, this number is programmed into either the external controller or the implantable stimulator.

A constant-voltage pulse design teaches against prevailing preferred designs for vagus nerve stimulators. Thus, constant-voltage pulses are used in cardiac pacemakers, deep brain stimulation, and some implantable neuromodulators for treatment of incontinence and chronic pain, but constant-current pulses are used for cochlear implants and vagus nerve stimulators [D. PRUTCHI and M. Norris Stimulation of excitable tissues. Chapter 7, pp. 305-368. In: Design and development of medical electronic instrumentation. Hoboken: John Wiley & Sons, 2005]. In the latter applications, the constant current design is said to be preferred because slight variations in stimulator-to-nerve distance change the ability of the constant-voltage pulse stimulator to depolarize the nerve, which is less of a problem with constant-current pulse stimulators. With the constant current design, the stimulation thresholds stay more or less constant even with changing electrode impedance and ingrowth of tissue into the neural interface [Emarit RANU. Electronics. Chapter 10, pp. 213-243. In: Jeffrey E. Arle, Jay L. Shils (eds). Essential Neuromodulation. Amsterdam, Boston: Academic Press. 2011]. For example, the BION stimulators described in the background section of the present application generate only constant current pulses.

In some embodiments of the present invention, a constant voltage pulse is used because it can be produced with a simpler circuit that consumes less power, as compared with constant pulse current circuits. The above-mentioned potential problem with variation in stimulator-to-nerve distance is addressed by anchoring the stimulator to the vagus nerve. Furthermore, the problem may be circumvented to some extent in the present invention by coating the stimulator's electrodes with a very thin layer of poorly conducting material. This is because the presence of a poorly conducting boundary layer surrounding the stimulator minimizes the differential effects of conductivity variations and electrode location during constant current and constant voltage stimulation [Mark M. STECKER. Nerve stimulation with an electrode of finite size: differences between constant current and constant voltage stimulation. Computers in Biology and Medicine 34 (2004):51-94].

Additional circuit simplicity and minimized power requirements are accomplished in the embodiment shown in FIG. 1C by fixing the characteristics of the stimulation pulses, rather than by adding circuits that would allow the characteristics to be adjusted through use of external control signals. For example, the output pulses shown in FIG. 1C are shown to be generated using a pair of monostable multivibrators. The first multivibrator receives a trigger pulse from the control unit 330, resulting in a pulse of fixed duration. The second multivibrator is triggered by the falling edge of the first multivibrator's pulse, and the pair of pulses from the two multivibrators are combined with suitable polarity using a differential operational amplifier. Thus, in this example, the impulse generator 310 consists of the multivibrators and operational amplifier. The amplifier in turn presents the stimulation pulses to the electrodes 340. The time period that a monostable multivibrator remains in its unstable state (the pulse width) is a function of its component resistor and capacitor values, so if the pulse width can be preselected for a patient, the device can be designed using correspondingly fixed R and C values. On the other hand, if a variable pulse width is needed during preliminary testing with a patient, the multivibrator circuit can be made more complex, with the pulse width selected on the basis of coded signals that are transmitted to the impulse generator 310 via the control unit 330. Once the appropriate pulse width has been selected, a control signal may be sent from the control unit 330 to disable extraneous power consumption by the variable pulse-width circuitry. Proper pulse width is particularly important in stimulating nerve fibers having the appropriate diameters [see discussion below and SZLAVIK RB, de Bruin H. The effect of stimulus current pulse width on nerve fiber size recruitment patterns. Med Eng Phys 21(6-7,1999):507-515].

It is also understood that more complex pulses may also be preferred, which would require a correspondingly more complex circuitry and possibly additional power consumption, as compared with the circuit shown in FIG. 15C [JEZERNIK S, Morari M. Energy-optimal electrical excitation of nerve fibers. IEEE Trans Biomed Eng 52(4,2005):740-743; Wongsarnpigoon A, Woock J P, Grill W M. Efficiency analysis of waveform shape for electrical excitation of nerve fibers. IEEE Trans Neural Syst Rehabil Eng 18(3,2010):319-328; FOUTZ TJ, Ackermann D M Jr, Kilgore K L, McIntyre C C (2012) Energy efficient neural stimulation: coupling circuit design and membrane biophysics. PLoSONE 7(12): e51901. doi: 10.1371/journal.pone.0051901, pp. 1-8; McLEOD KJ, Lovely D F, Scott R N. A biphasic pulse burst generator for afferent nerve stimulation. Med Biol Eng Comput 25(1,1987):77-80].

The control unit 330 in FIG. 1C is shown to exercise its control only by presenting trigger pulses to the impulse generator 310. In this example, the train of pulses appearing across the electrodes 340 is determined only by the timing of the sequence of trigger pulses. The trigger pulses are themselves encoded in the signal that is transmitted from controller 370 in FIG. 1A, shown in FIG. 1C as "RF signal with encoded trigger pulse." The trigger pulses are extracted and reconstructed from the transmitted signal by an RF demodulator in the control unit 330. There are many methods for transmitting and decoding such control signals, and the present invention may be designed to use any of them [Robert PUERS and Jef Thoné. Short distance wireless communications. Chapter 7, pp. 219-277, In: H.-J. Yoo, C. van Hoof (eds.), Bio-Medical CMOS ICs. New York: Springer, 2011]. Because the timing of pulses is determined by the trigger pulses emanating from the transmitted signal, the circuit shown in FIG. 1C does not even need a clock, thereby reducing its power requirements. However, in other embodiments a clock may be included as part of the timing circuitry. It is understood that in order to command a pulse of the treatment signal and switch that pulse to the electrodes, it is possible to use a control RF signal having a different frequency than the one used to provide power, or encode the command based on variation in the RF signal's amplitude, pulse width and/or duration.

The transmitted RF signal is received by an antenna 360, and the signal provides power for the stimulation device 300, in addition to the control signals. The power is provided by the power source 320 in FIG. 1C. As shown there, energy from the transmitted RF signal (beamed power) is accumulated in a storage capacitor, which is eventually discharged in conjunction with the creation of stimulation pulses that are applied to the electrodes 340. In addition to the beamed power, there may also be scavenged power, which arises from the reception of ambient electromagnetic radiation by the antenna 360. Special circuits and antennas may be used to scavenge such ambient electromagnetic radiation [Soheil RADIOM, Majid Baghaei-Nejad, Guy Vandenbosch, Li-Rong Zheng, Georges Gielen. Far-field RF Powering System for RFID and Implantable Devices with Monolithically Integrated On-Chip Antenna. In: Proc. Radio Frequency Integrated Circuits Symposium (RFIC), 2010 IEEE, Anaheim, Calif., 23-25 May 2010, pp. 113-116]. Power scavenging may be most appropriate in a hospital setting where there is significant ambient electromagnetic radiation, due to the use there of diathermy units and the like [FLODERUS B, Stenlund C, Carlgren F. Occupational exposures to high frequency electromagnetic fields in the intermediate range (>300 Hz-10 MHz). Bioelectromagnetics 23(8,2002):568-577]

The stimulator circuit comprises either a battery or a storage device, such as a capacitor, for storing energy or charge and then delivering that charge to the circuit to enable the circuit to generate the electrical impulses and deliver those impulses to the electrodes. The energy for the storage device is preferably wirelessly transmitted to the stimulator circuit through a carrier signal from the external controller. In the preferred embodiments, the energy is delivered to the energy storage device between electrical impulses. Thus, the energy is not being delivered in "real-time", but during the periods when the pulse is not being delivered to the nerve or during the refractory period of the nerve. For example, a typical electrical impulse may be ON for about 200 uS and then OFF for about 39,000 uS. The energy is delivered during this longer OFF time, which enables the system to use a much smaller signal from the external generator. The external generator delivers the carrier signal over the OFF period to charge the energy storage device, which then releases this energy or charge to the remainder of the circuit to deliver the electrical impulse during the 200 uS ON time.

Transmitting energy to the storage device in between the electrical impulses provides a number of advantages. First, it increases the length of time that the electrical energy can be delivered to charge the storage device. This reduces the strength of the signal required to deliver the electrical energy to the storage device, thereby reducing the overall power requirements of the external controller and reducing the complexity of the stimulator circuitry. In addition, it enhances the safety of the device because it reduces the risk that uncontrolled environmental RF energy will create an electrical connection between the nerve and the charged energy. Since the storage device is receiving electrical energy between electrical impulses, there is no electrical connection between the stimulator circuit and the nerve as the storage device is charged. This reduces the risk of the electrical energy being accidently applied to the nerve.

In order to power the impulse generator and demodulation circuits, the power source 320 in FIG. 1C makes use of a voltage regulator, the output from which is a stable voltage V. The circuits that may be selected for the voltage regulator comprise those described by BOYLESTAD [Robert L BOYLESTAD and Louis Nashelsky. Power Supplies (Voltage Regulators). Chapter 18, pp. 859-888. In: Electronic devices and circuit theory, 8th ed. Upper Saddle River, N.J.: Prentice Hall, 2002].

In preferred embodiments of the present invention, the parameters of fixed stimulation pulses are generally as follows. The shape of the pulse is square, sine, triangular or trapezoidal with negative voltage return to eliminate DC bias. The electrical impulse will typically have a frequency of between about 1-500 Hz, preferably about 1 to 50 Hz, and more preferably about 10-35 Hz. In an exemplary embodiment, the frequency for the impulse received by the nerve is about 25 Hz. The preferred fixed voltage received by the nerve is between about 1-20 V and will typically vary depending on the size and type of electrode and the distance between the electrode and the nerve. In certain embodiments where the nerve is directly attached to the nerve (or implanted adjacent to the nerve), the fixed voltage is preferably about 1 to 4 volts, more preferably about 2 volts. In other embodiments, wherein the electrode is, for example, injected into the patient and implanted outside of the sheath, the voltage is preferably between about 7-15 volts and more preferably about 10 V. In embodiments wherein the current is fixed or held constant, the preferred fixed current is about 0.5 mA to about 20 mA. Similar to voltage, the fixed current will vary depending on the size and type of electrode and its distance from the nerve. In those embodiments where the electrode is adjacent to, or on, the nerve, the current is preferably about 0.5 to 5 mA and more preferably about 3.5 mA. In those embodiments, where the electrode is spaced from the nerve (just as an injectable electrode outside of the sheath), the current is preferably about 7-15 mA and more preferably about 10 mA. The pulse duration is preferably between about 50 to 1000 uS The disclosed system and method include a number of benefits. The implanted signal generator can be much smaller than a traditional implanted generator. The surgery to implant this system can be done under local anesthesia on an outpatient basis in a non-hospital setting resulting in faster recovery and less scarring. Furthermore, since there is no implanted battery, the patient does not need additional surgeries to replace batteries, which is especially important if the patient has a treatment protocol that requires treatments involving significant power and duration. Also, the limited circuitry implanted in the body will be more reliable than traditional implanted generators. Because the treatment is powered and controlled from outside the body, changes to the treatment protocol can be made quickly and easily. In the event of an emergency, the patient or caregiver can quickly turn-off or remove the power/control unit to stop treatment.

The stimulator circuit is novel in that it removes one (or more) elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of pulses, but by then controlling the number and timing of pulses that the nerve experiences, in order to achieve the same physiologically desirable level of nerve stimulation. In essence, this invention is using an adjustable number of fixed voltage (or current) pulses with fixed duration to elicit desired changes in nerve response.

The electrode and signal generator are primarily, but not exclusively, intended for stimulation of the SPG and other cranial nerves, for conditions that include primary headache, such as cluster headache, migraine and the like. In those applications, the typical signal would be square or sine pulses of fixed amplitude approximately 2 Volts, where each pulse has a fixed duration of about 200 uS. Typically 5 of these pulses would be produced every 40 mS to produce an effective 25 Hz signal. The selection of these waveform parameters is discussed more fully below.

The control unit 330 controls the impulse generator 310 to generate a signal for each of the device's electrodes. The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals, analog-to-digital converters for digitizing externally supplied analog signals such as physiological signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback, including biofeedback, measured from externally supplied physiological or environmental signals. Alternatively, the control unit 330 may have a compact and simple structure, for example, wherein the user may operate the system using only an on/off switch and power control wheel or knob. In a section below, a preferred embodiment is described wherein the stimulator housing has a simple structure, but other components of the control unit 330 are distributed into other discrete devices.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurło, Przemysław Płonecki, Jacek Starzyński, Stanisław Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied. The preferred pulse parameters are described in a later section of this application.

The invention also contemplates an electrode configuration in which all electrode contacts connected as anodes may have a different voltage, and all electrode contacts connected as cathodes may have a different voltage. For the electrodes implanted parallel to the vagus nerve, this may occur when the anode and cathode voltages for different electrodes change rapidly in sequence from one end of the device to the other, in an attempt to entrain or inhibit action potentials of certain fibers of the nerve bundle. This may be done, for example, so as to stimulate particular afferent versus efferent fibers. In this example, the temporal sequence of electrode activation by the device may be in the orthodromic or antidromic direction for any particular fiber within the vagus nerve.

FIG. 2 illustrates different electrode assemblies that are contemplated by the invention. In FIG. 2A, the modulating device 200 comprises four electrodes 240 that are separated and surrounded by electrically insulating material 205. As shown, the device has the style of a paddle, so that the stimulation occurs preferentially on the side of the paddle with exposed electrodes 240. The device has attached extension tubing 201 with a central lumen 204 that is intended for the introduction of a stylet or other tool used during implantation of the device 200. In FIG. 2B, the modulating device 200 comprises eight electrodes 240 that are separated by electrically insulating material 205. The device also has attached extension tubing 201 with a central lumen 204. As shown, the device in FIG. 2B has the style of a cylinder, so that stimulation from the exposed electrodes 240 occurs symmetrically with respect to the axis of the cylinder.

FIG. 2C illustrates an exemplary electrode assembly 240 on the device 200 according to a preferred embodiment of the present invention. The device contains two electrodes in a cylindrical-style stimulator. As shown, electrode assembly 240 includes an active electrode 502 and a return electrode 504 coupled to the pulse generating circuits of the device 200. Active and return electrodes 502 and 504, respectively, are spaced a suitable distance to allow for the formation of an electromagnetic field around electrode assembly 240 for modulation of nerve(s) at the target region (not shown). In this embodiment, electrodes 502 and 504 are spaced from each other with insulating material 205 by about 5-50 mm, preferably between about 10-20 mm. As shown, the electrodes are exposed along only part of the diameter of the cylinder, so as to be able to direct the formed electromagnetic field pulses in a particular direction, namely, towards the nerve that they are intended to stimulate.

Although there are a number of sizes and shapes that would suffice to implement electrodes 502 and 504, by way of example, electrodes may be between about 1.0-1.5 mm long (such as 1.2 mm), may have an outside diameter of between about 2.6-2.85 mm (such as 2.7 mm), and may have an inside diameter of between about 2.5-2.75 mm (such as 2.7 mm). A suitable electrode may be formed from Pt—IR (90%/10%), although other materials or combinations or materials may be used, such as platinum, tungsten, gold, copper, palladium, silver, or the like.

Those skilled in the art will also recognize that a variety of different shapes and sizes of electrodes may be used. By way of example only, electrode shapes according to various aspects of the present invention can include ball shapes, twizzle shapes, spring shapes, twisted metal shapes, annular shapes, solid tube shapes, flat shapes or the like. Alternatively, the electrode(s) may comprise a plurality of filaments, rigid or flexible brush electrode(s), coiled electrode(s) or the like. Alternatively, the electrode may be formed by the use of formed wire (e.g., by drawing round wire through a shaping die) to form electrodes with a variety of cross-sectional shapes, such as square, rectangular, L or V shaped, or the like.

The device shown in FIG. 2C differs from the devices shown in FIGS. 2A and 2B in that it contains a connecting piece 210 that is interposed between the part of the device 200 containing the electrodes 240 and the tubing 201. The purpose of the connecting piece 210 is to make it easy to disconnect the tubing from the stimulator device 200 once the device is finally implanted. The connecting piece 210 shown in FIG. 2D contains a male part 211 and a female part 212 that interconnect with one another when the tubing 201 is being used to position the device 200. The male part is permanently connected to the tubing, and the female part is connected permanently to the device 200. The parts are held together with thread or wire 213 that is threaded through aligned holes in the insert 215 of the male part 211 and walls of the groove 216 of the female part 212. As shown in FIG. 2E, when the thread is pulled out, the interconnecting male part 211 disconnects from the female part 212 when the tubing 201 is pulled.

An alternate connecting piece 210 is shown in FIG. 2F. In that case, a male part 218 and a female part 219 interconnect with one another when the tubing 201 is being used to position the device 200. The male part is permanently connected to the tubing 201, and the female part is connected permanently to the device 200. The pieces are mated through an insert 215 in the male part 218 that is situated in a groove 216 of the female part 219. In this case, the pieces are held together magnetically, rather than by a thread through aligned holes. As shown, the male part 218 is an electromagnet that is powered when the tubing 201 is being used to position the stimulator 200. The electromagnet comprises a coil wound around a core of ferromagnetic material such as soft iron. The magnetic field that the electromagnet produces holds the female part 219 to the male part 218, because the female part is either a permanent magnet or is made of soft-magnetic material, i.e., it becomes magnetic in the presence of the magnetic field produced by the electromagnet (e.g., a piece of iron). When current through windings of the electromagnet is turned off, the male and female pieces will separate when the tubing 201 is pulled.

An advantage of using the connecting piece 210 shown in FIG. 2F is that it allows the device 200 to be re-positioned magnetically after the tubing 201 and its attached male part 218 have been removed. This is because a magnetic field applied externally to the patient may be used to manipulate the location and orientation of the female part 219 in FIG. 2F (and therefore the stimulator 300 to which the female part 219 is permanently attached), whether the female part is a permanent magnet or is made of soft-magnetic material [GILLIES, G. T., Ritter, R. C., Broaddus, W. C., Grady, M. S., Howard, M. A., and McNeil, R. G. Magnetic manipulation instrumentation for medical physics research. Review of Scientific Instruments 65(3,1994):533-562; Jake J. ABBOTT, Olgaç

Ergeneman, Michael P. Kummer, Ann M. Hirt, and Bradley J. Nelson. Modeling magnetic torque and force for controlled manipulation of soft-magnetic bodies. IEEE Transactions on Robotics 23(6, 2007):1247-1252].

The requirements for device re-positioning would be based upon images of the device 200 in its originally implanted site and orientation, as compared with images of the device in its present, presumably non-ideal, site or orientation. Such imaging may involve different potential imaging modalities, such as fluoroscopy or MRI. The preferred imaging methods involve ultrasound, as described below in connection with the use of ultrasound imaging to implant the stimulator device. In order to explain the invention's methods for imaging and implanting the device 200 into the neck of the patient, it is first necessary to summarize the relevant anatomy of the neck, as follows.

Figure 8A:
FIGS. 8A-8D illustrate various configurations of antennas within the stimulation device of the invention.
Figure 8B:
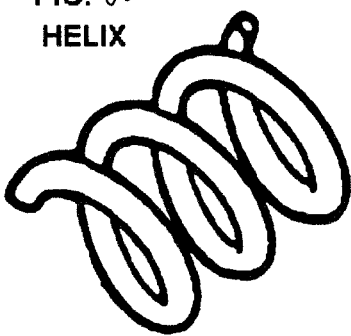
Figure 8C:
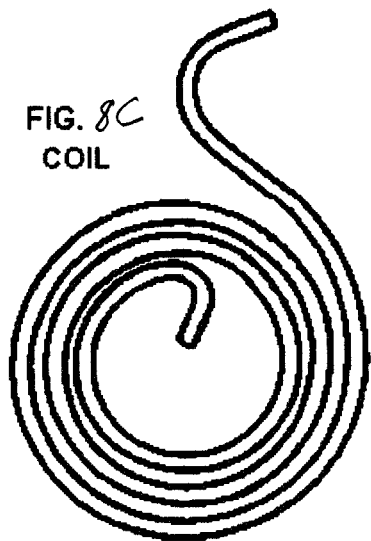
Figure 8D:
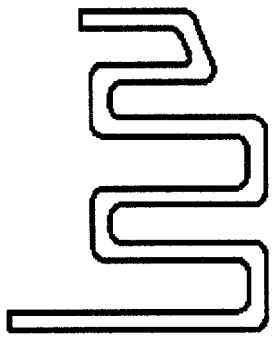

In the present application, a dipole configuration for the stimulator's antenna is not ideal because use of a straight antenna would limit its length to the dimension of the anatomical space into which the antenna is to be situated. To achieve a longer antenna length and yet be able to fit the stimulator into the intended anatomical site, in the preferred embodiment of the present invention, the antenna (stimulator) is not a straight dipole. It is instead a helical antenna (FIG. 8B), a coiled antenna (FIG. 8C), or a meandering antenna (FIG. 8D), or has some other nonlinear conformation.

The present invention contemplates changing the geometry of the stimulator's antenna from a linear (classic dipole) configuration that can be passed through a needle to the vicinity of the SPG, into another shape, such as the meandering configuration shown in FIG. 8. As shown in FIG. 8A, the stimulator is initially a 40 mm linear stimulator (antenna) that can receive significant power from an external radio source. As the stimulator is pushed through a needle to the vicinity of the SPG, it is bent near its ultimate anatomical location to achieve a more compact meandering conformation (successively FIG. 9B through 9G). The bending is performed using endoscope instruments (clips, forceps, graspers, etc.) that may make use of loops that are attached to the stimulator (see FIGS. 9A-9G). The loops may also be used to suture the meandering stimulator to its ultimate anatomical location (e.g., FIG. 9H). Alternatively, the endoscopic instruments (clips, forceps, graspers, etc.) may simply position the meandering stimulator to the desired location, and the stimulator is then glued in place. It is understood that after its meandering conformation has been constructed, the stimulator is translocated and reoriented along the mucosal surface. As it is moved about, the stimulator is stimulated via the external radio source to determine the position and orientation that achieves an optimal response on the part of the patient. After that optimal placement is determined, it is then glued or sutured in place.

The previous paragraph describes use of the stimulator in the first (noninvasive) embodiment that was described above. If the second or third embodiments are used (FIGS. 7A-7D), an anchor is first placed in the vicinity of the SPG, and the stimulator is then attached to the anchor by sutures or some other convenient method. Those embodiments may also use long-antenna stimulators (e.g., 40 mm length) that are bent into a compact conformation.

If the stimulator is to be inserted into the pterygopalatine (sphenopalatine) fossa, the length of the stimulator may be decided during surgery. For example, in the fourth embodiment described above, a lead blank is inserted into the fossa to create a wormhole for the stimulator. When the lead blank cannot be inserted any further into the fossa without significant resistance from some structure within the fossa, then the appropriate length of the stimulator is determined by the length of the wormhole at that point. If the pterygopalatine (sphenopalatine) fossa is surgically opened and inspected, as in the fifth embodiment that was described above, the appropriate length of the stimulator will be determined by the surgeon after deciding where the stimulator is to be placed.

In the present disclosure, the second, external transmitting antenna, which serves as the source of the stimulator's power and stimulation waveform, is preferably situated within a handheld device that may be placed near, and pointed towards, the patient's nose, whenever it is desired to stimulate the SPG. Thus, the handheld device serves to control operation of the stimulator and might resemble a typical remote control device or a smartphone. Parameters for the stimulation (On/Off, power level, frequency, etc.) are adjusted on the handheld controller using pushbuttons or a touchscreen, and the menu for modifying parameters is preferably visible on the device's screen. The handheld radio control device may be powered by a battery or any other convenient power source.

Communication between the handheld controller (transmitting antenna) and the stimulator within the patient preferably makes use of radio communication within unlicensed ISM frequency bands (260-470 MHz, 902-928 MHz, 2400-2.4835 GHz). Components of the RF system in the handheld controller typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006; Texas Instruments. TI Low Power RF. Designer's Guide to LPRF. Texas Instruments, Post Office Box 655303, Dallas, Tex. 75265, pp. 1-64, 2010].

Figure 10A:
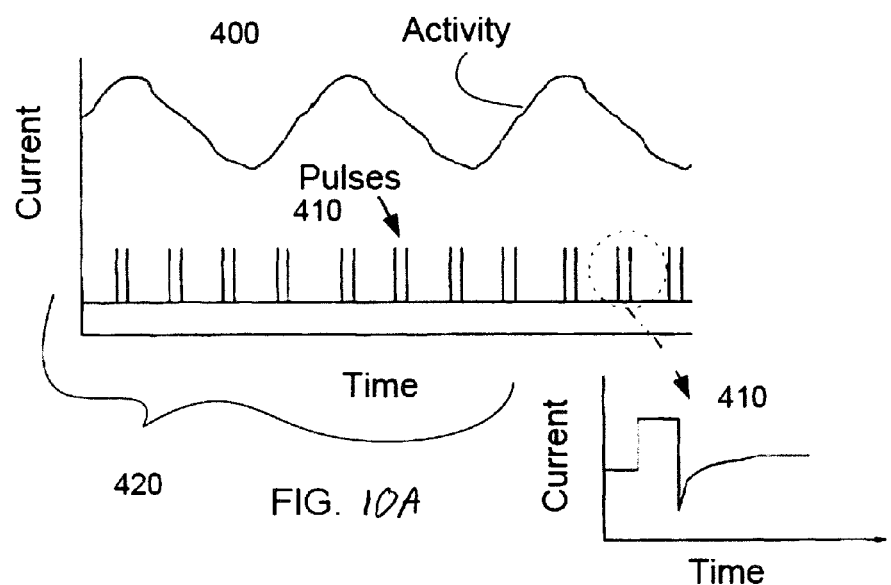
FIGS. 10A-10C illustrate waveforms for the electrical impulses generated by the devices and methods of the present invention.
Figure 10B:
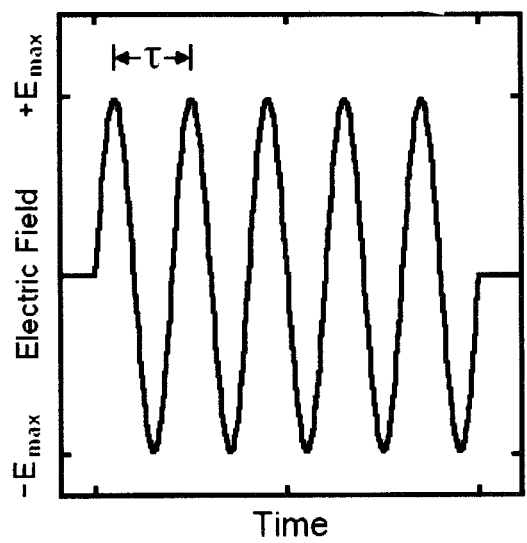
Figure 10C:
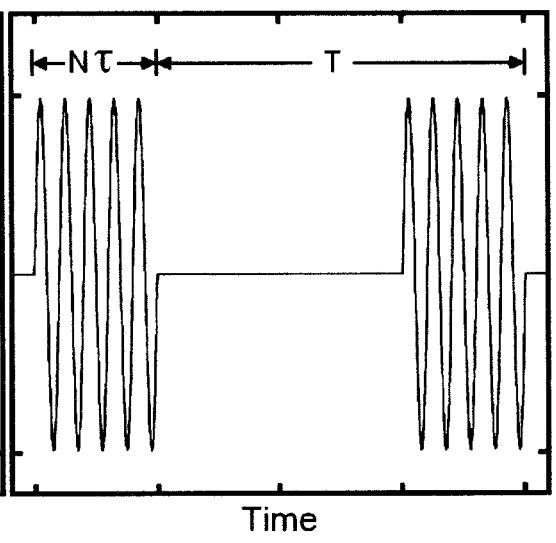

A typical signal waveform that may be transmitted to the stimulator by the handheld controller and transmitting antenna is shown in FIGS. 10A-10C, in which the signal is shown on a short (A) and long (B) time scale. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 10B to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, Emax, etc., but in that case the stimulator would then have to construct the waveform from the transmitted parameters.

Particular stimulation waveforms, such as the one shown in FIGS. 10A-10C, may be used to selectively stimulate certain nerve fibers within the SPG (such as fibers of type A and B), and avoid stimulation of other fiber (such as fibers of type C). This feature was described in a recent co-pending, commonly assigned application entitled, NON-INVASIVE VAGUS NERVE STIMULATION TO TREAT BRONCHIAL CONSTRICTION, which has previously been incorporated by reference.

Another embodiment of the invention includes a docking station that may also be used as a recharging power supply for the stimulator housing. The docking station may send/receive data to/from the stimulator housing, and may send/receive data to/from databases and other components of the system, including those that are accessible via the internet. Thus, prior to any particular stimulation session, the docking station may load into the stimulator parameters of the session, including stimulation waveform parameters.

In a preferred embodiment, the docking station also limits the amount of stimulation energy that may be consumed by the patient in the stimulation session, by charging the stimulator's rechargable battery with only a specified amount of releasable electrical energy. Note that this is generally different than setting a parameter to restrict the duration of a stimulation session. As a practical matter, the stimulator may therefore use two batteries, one for stimulating the patient (the charge of which may be limited by the docking station) and the other for performing other functions such as data transmission. Methods for evaluating a battery's charge or releasable energy are known in the art, for example, in U.S. Pat. No. 7,751,891, entitled Power supply monitoring for an implantable device, to ARMSTRONG et al. Alternatively, control components within the stimulator housing may monitor the amount of stimulation energy that has been consumed during a stimulation session and stop the stimulation session when a limit has been reached, irrespective of the time when the limit has been reached. A more complete description of a suitable docking station can be found in commonly-assigned, co-pending U.S. patent application Ser. No. 13/858,114, filed Apr. 6, 2013, the complete disclosure of which is incorporated herein in its entirety for all purposes.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of a radio frequency system in the devices typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard.

The stimulating and/or modulating impulse signal preferably has a frequency, an amplitude, a duty cycle, a pulse width, a pulse shape, etc. selected to influence the therapeutic result, namely, stimulating and/or modulating some or all of the transmissions of the selected nerve. For example, the frequency may be about 1 Hz or greater, such as between about 15 Hz to 100 Hz, more preferably around 25 Hz. The modulation signal may have a pulse width selected to influence the therapeutic result, such as about 1 microseconds to about 1000 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts.

In other embodiments, the waveform comprises bursts of sinusoidal pulses, as shown in FIGS. 10B and 10C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 10C to make the bursts discernable). When these exemplary values are used for T and tau, the waveform contains significant Fourier components at higher frequencies (1/200 microseconds=5000/sec), as compared with those contained in transcutaneous nerve stimulation waveforms, as currently practiced.

It is understood that the electrical stimulation of the SPG may be designed to produce irreversible effects (ablation), rather than reversible effects, if the frequency of stimulation is significantly greater than 10 kHz and/or other stimulation parameters are used [LEE RC, Zhang D, Hannig J. Biophysical injury mechanisms in electrical shock trauma. Annu Rev Biomed Eng 2 (2000):477-509].

Finally, the present disclosure contemplates stimulating nerves other than those within the SPG. In particular, the stimulator may be placed in the vicinity of any cranial nerve that is accessible endoscopically through the nose. In general, particular cranial nerves become increasingly difficult to access endoscopically through the nose as the distance from nasal passages increases. The location of the SPG is relatively close to the nasal passages, but others such as the vagus nerve lie towards the back of the head. Some nerves may be conveniently stimulated at one location but less conveniently at another location. For example, the maxillary nerve (V2) may be stimulated at or near the SPG. For the treatment of pain, including headache pain, one may particularly wish to stimulate the mandibular nerve (V3), the trigeminal ganglion, the trigeminal nerve proper (V), and the vagus nerve.

The endonasal corridors through which such intracranial targets may be surgically accessed are reviewed by AINSWORTH and colleagues [Tiffiny AINSWORTH, Belachew Tessema, and Seth M. Brown. Overview of endonasal corridors to intracranial targets. Operative Techniques in Otolaryngology 22 (2011):194-199]. CAVALLO and colleagues describe how all twelve of the cranial nerves are accessible [Luigi M. CAVALLO, Andrea Messina, Paolo Cappabianca, Felice Esposito, Enrico De Divitiis, Paul Gardner, and Manfred Tschabitscher. Endoscopic Endonasal Surgery of the Midline Skull Base: Anatomical Study and Clinical Considerations. Neurosurg Focus 19(1,2005), pp. 1-29].

Other reviews that provide more details of the endonasal surgical technique are by CAPPABIANCA and by EMMANUEL [P. CAPPABIANCA, L. M. Cavallo, F. Esposito, O. DeDivitiis, A. Messina, and E. DeDivitiis. Extended endoscopic endonasal approach to the midline skull base: the evolving role of transsphenoidal surgery. pp. 151-199 in: Advances and Technical Standards in Neurosurgery, Vol 33, Edited by J. D. Pickard, N. Akalan, C. Di Rocco, et al. Vienna: Springer, 2008; Jouanneau EMMANUEL, Messerer Mahmoud, Berhouma Moncef (2011). Endoscopic Endonasal Skull Base Surgery: Current State of the Art and Future Trends, Chapter 1, pp. 3-38, In: Advances in Endoscopic Surgery, Cornel Iancu, ed., Rijeka, Croatia: InTech (2011)].

Thus, the present invention contemplates the insertion of the stimulator described above in the vicinity of nerves such as the mandibular nerve (V3), the trigeminal ganglion, the trigeminal nerve proper (V), and the vagus nerve. The insertion is made during endoscopic endonasal surgery, in the manner described above as the fifth embodiment of the SPG stimulator insertion method. Considering that endoscopic endonasal surgery involving such nerves is most commonly performed in connection with the removal of a nearby tumor, patients with such tumors may be the most likely candidates for the disclosed stimulation of the cranial nerves. In these embodiments, the wirelessly powered implantable stimulator described above can be implanted adjacent to or near the target nerve during the endoscopic procedure.

Although the preferred embodiments of the invention are as described above, it is understood that one may also modify the capabilities of the device. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, the pulse command could optionally have an address or other identifier associated with it so that only a particular signal generator would be activated. This would allow a patient to have multiple implanted signal generators in the body with each responding to its own command from the same or multiple power/control units. Another option would be to have circuitry or a processor in the implanted signal generator that could communicate a signal back to the power/control unit. This signal could contain status information such as voltage, current, number of pulses applied or other applicable data. The antennae and RF signals in this system could also be replaced by closely coupled coils of wire and lower frequency signals that are inductively coupled through the body.

The invention claimed is:

1. A system for modulating a cranial nerve to treat a medical condition of a patient comprising:
   a stimulation device comprising one or more electrodes configured for advancement through a nostril of a patient to a target site adjacent to or near the cranial nerve and one or more antennas;
   a power source configured for positioning externally to a patient and further configured to transmit electrical energy wirelessly through an outer skin surface of the patient to the stimulation device at the target site, wherein the one or more antennas are configured for receiving the electrical energy from the power source at the target site;
   a pulse generator coupled to the power source and the stimulation device and configured to apply one or more electrical impulses to the electrodes sufficient to modulate the cranial nerve.

2. The system of claim 1 wherein the cranial nerve is a sphenopalatine ganglion.

3. The system of claim 1 wherein the medical condition is primary headache.

4. The system of claim 1 wherein the medical condition is cluster headache.

5. The system of claim 1 wherein the antennas have a substantially non-linear configuration.

6. The system of claim 5 wherein the stimulation device further comprises an energy storage device for storing the electrical energy received by the antenna(s).

7. The system of claim 1 wherein the stimulation device is configured to be positioned adjacent to or near a mucosa area posterior to a middle turbinate of the patient.

8. The system of claim 1 further comprising one or more anchors configured to extend through a mucosa within a nose of the patient, the stimulation device being configured for positioning adjacent to the mucosa and coupled to the anchors.

9. The system of claim 1 further comprising one or more anchors configured to extend into a rigid structure within a nose of the patient, the stimulation device being configured for positioning adjacent said rigid structure and coupled to the anchors.

10. The system of claim 1 further comprising a lead blank configured for advancement through a mucosa of a sphenopalatine fossa to a target site adjacent to or near the cranial nerve, wherein the lead blank comprises a distal tip configured to generate a path for the stimulation device to follow to the target site.

11. A method for modulating a cranial nerve to treat a medical condition in a patient comprising:
    advancing one or more electrodes through a nostril of the patient to a target site adjacent to or near a cranial nerve;
    generating one or more electrical impulses sufficient to modulate the cranial nerve; and
    wirelessly transmitting the one or more electrical impulses from a power source external to the patient through an outer skin surface of the patient to the electrodes at the target site.

12. The method of claim 11 wherein the cranial nerve is a sphenopalatine ganglion.

13. The method of claim 11 wherein the medical condition is primary headache.

14. The method of claim 11 wherein the medical condition is cluster headache.

15. The method of claim 11 further comprising advancing one or more antennas with the electrodes to the target site, the antennas having a substantially non-linear configuration and wherein the wirelessly transmitting step is carried out by transmitting the electrical impulses to the antennas.

16. The method of claim 15 further comprising wirelessly transmitting electrical energy to the antennas, storing the electrical energy and using the electrical energy to apply the electrical impulses to the cranial nerve.

17. The method of claim 11 wherein the target site is adjacent to or near a mucosa area posterior to a middle turbinate of the patient.

18. The method of claim 11 further comprising securing the electrodes adjacent to a mucosa within the nose of the patient.

19. The method of claim 18 wherein the securing step is carried out by driving one or more anchors through the mucosa and attaching the electrodes to the anchors.

20. The method of claim 18 wherein the securing step is carried out by driving one or more anchors into a rigid structure within the nose of the patient and attaching the electrodes to the anchors.

21. The method of claim 11 further comprising:
    advancing a lead blank through the nostril of the patient and through a mucosa of a sphenopalatine fossa to the target site adjacent to or near the cranial nerve to generate a path for the electrodes; and
    advancing the electrodes along the path to the target site.

* * * * *